(12) United States Patent
Jang

(10) Patent No.: US 8,801,846 B2
(45) Date of Patent: Aug. 12, 2014

(54) SELF-NEUTRALISING TYPE OF CALCIUM HYDROXIDE PREPARATION FOR USE IN DENTISTRY

(76) Inventor: Sung Wook Jang, Seoul (KR)

( * ) Notice: Subject to any disclaimer, the term of this patent is extended or adjusted under 35 U.S.C. 154(b) by 166 days.

(21) Appl. No.: 12/989,349

(22) PCT Filed: Apr. 24, 2009

(86) PCT No.: PCT/KR2009/002163
§ 371 (c)(1),
(2), (4) Date: Oct. 22, 2010

(87) PCT Pub. No.: WO2009/131415
PCT Pub. Date: Oct. 29, 2009

(65) Prior Publication Data
US 2011/0041727 A1 Feb. 24, 2011

(30) Foreign Application Priority Data
Apr. 24, 2008 (KR) .................. 10-2008-0038387

(51) Int. Cl.
*A61K 6/04* (2006.01)
(52) U.S. Cl.
USPC .............................. 106/35; 106/705; 106/709
(58) Field of Classification Search
USPC .......................................... 106/35, 705, 709
See application file for complete search history.

(56) References Cited

U.S. PATENT DOCUMENTS 2,549,180 A    4/1951  Jack De Ment et al.

FOREIGN PATENT DOCUMENTS

| WO | 2002015848 A2 | 2/2002 |
| WO | 02056838 A1 | 7/2002 |
| WO | 2005039509 A1 | 5/2005 |

OTHER PUBLICATIONS

International Search Report. Korean Intellectual Property Office. Nov. 25, 2009.

*Primary Examiner* — Carol M Koslow

(57) ABSTRACT

The present invention relates to a self-neutralising type of calcium hydroxide ($Ca(OH)_2$) preparation for use in dentistry. More specifically, it relates to a self-neutralising type of calcium hydroxide preparation which is formulated in such a way that it can be used in dentistry by being mixed, in a cement clinker, with an active siliceous substance, bismuth oxide ($Bi_2O_5$), silica, sulphur trioxide and aluminum oxide/ferric oxide and the like. One aspect of the present invention provides a self-neutralising type of calcium hydroxide preparation comprising an active siliceous substance and bismuth oxide, and this self-neutralising type of calcium hydroxide preparation is characterized in that it comprises silica, sulphur trioxide and aluminum oxide/ferric oxide.

1 Claim, No Drawings

SELF-NEUTRALISING TYPE OF CALCIUM HYDROXIDE PREPARATION FOR USE IN DENTISTRY

PRIORITY

The present application is a national stage filing under 35 U.S.C. §371 of PCT Application number PCT/KR2009/002163, filed on Apr. 24, 2009, which claims priority to Korean Patent Application No. 10-2008-0038387, filed on Apr. 24, 2008, the disclosures of which are hereby incorporated by reference in their entireties.

TECHNICAL FIELD

The present invention relates to a self-neutralising type of calcium hydroxide ($Ca(OH)_2$) preparation for use in dentistry, and more particularly, to a self-neutralising type of calcium hydroxide preparation prepared by mixing to a cement clinker an active silica material, bismuth oxide ($Bi_2O_5$), silica, sulfur trioxide and aluminum oxide/red oxide ($Fe_2O_3$) so that it can be used for the purpose of dental treatment.

BACKGROUND ART

We call it dental caries the phenomenon of components on the surface of a tooth such as calcium and phosphor being melted by acid and components such as protein being worn out to create a hole in the tooth. Herein, such tooth is called a decayed tooth.

When dental caries has progressed to some extent, a common root canal therapy or a direct or indirect pulp capping therapy may be applied. In many cases, a root canal therapy is performed, but it disadvantageously requires a long surgical operation time, complicated operations and high treatment cost. Therefore, it is believed that if a direct or indirect pulp capping therapy can be stably applied with a high success rate, many patients could be free from fear for a dental treatment, pain by extensive tooth elimination and high treatment cost. This is why researches on a direct or indirect pulp capping therapy are being widely performed.

DISCLOSURE

Technical Problem

When dental caries has extensively progressed on a tooth (esp., a milk tooth), a pulpotomy is performed in common, for which medicine such as formocresol and ferric sulfate is utilized. However, formocresol, the frequently used medicine, has demerits in that it contains a carcinogenic component and exhibits strong cell virulence, and ferric sulfate, the recently studied medicine, is not widely used yet because it also has demerits of cell virulence and root resorption.

Recently, a pulp capping therapy using a Mineral Trioxide Aggregate (MTA) has been extensively studied, but it is not appropriate for neutralising calcium hydroxide produced during hydration, and thus, induces hydration heat and requires too long a time for neutralisation. This makes the pulp capping therapy (esp., the direct pulp capping therapy) using an MTA less applicable. Still, many efforts are being made to advance the above therapy because of its merits mentioned later.

Meanwhile, examples of a calcium hydroxide preparation used as a filler for dental treatment include a self-reacting calcium hydroxide preparation and a photo-reacting calcium hydroxide preparation. However, a self-reacting calcium hydroxide preparation and a photo-reacting calcium hydroxide preparation are not widely used because they show low compression strength, low chemical resistance and cell virulence, which generally lowers a success rate for a direct pulp capping therapy. Thus, they are limited to use for an indirect pulp capping therapy.

Further, an oxidized eugenol preparation such as an IRM is used for a direct pulp capping therapy, but it shows a low success rate and is not popular in an actually clinical situation.

Accordingly, a therapy using an MTA mentioned as above is still a subject for various researches for the reasons that an MTA is advantageous in its bioaffinity and has a capability of guided regeneration for an alveola bone and accelerating formation of secondary dentine and cement, unlike an existing calcium hydroxide preparation, when it is used for the purpose of treating a damaged root canal.

However, it is found that an MTA has drawbacks as follows: (i) it takes long to harden (e.g., it requires three or more hours for initial hardening), (ii) it shows poor operability (i.e., it is easily washed out by water, a saline solution or blood even before being hardened, shows a low flow feature, and makes an operation hard), (iii) it generates a high level of hydration heat, and (iv) it causes continuous secretion of calcium hydroxide. Therefore, an MTA has been restrictively used in such a case that a bored portion of a dental root needs to be closed up or an endodontic treatment for a tooth (e.g., a tooth having an uncompleted root tip) is necessary, which can be hardly recovered with existing therapies and preparations. In addition, the high price of an MTA is one of the reasons that its usage is limited.

Therefore, it is required to develop a novel preparation for overcoming the aforementioned problems.

Technical Solution

It is an objective of the present invention to replace the existing complicated therapies with a simple and effective one.

Another objective of the present invention is to provide a self-neutralising calcium hydroxide preparation for use in dentistry, which hardens quickly, has excellent chemical resistance, and is solidified in a saline solution.

Yet another objective of the present invention is to provide a self-neutralising calcium hydroxide preparation for use in dentistry, which is advantageous for treatment for a damaged tooth, guides formation of secondary dentine and cement of a tooth, and is capable of preserving vitality of dental pulp (esp., dental pulp of a milk tooth) even when the dental pulp is cut.

Advantageous Effects

The self-neutralising calcium hydroxide preparation for use in dentistry in accordance with the present invention has an excellent hardening feature and chemical resistance and is filled in a tooth in combination with a saline solution, and thus, is useful as a filler for dental treatment.

Further, in accordance with the present invention, a filler for dental treatment is obtained that may be applied to a direct or indirect pulp capping therapy and a pulp cutting therapy for a milk tooth, which cannot be easily operated with the existing techniques, and usefully to treatment for an uncompleted infected root canal, which has been enabled only with the existing MTA.

Best Mode

The compositions of the present invention for achieving the aforementioned objectives are presented as follows:

In accordance with one aspect of the present invention, there is provided a self-neutralising type of calcium hydroxide preparation for use in dentistry, including an active silica material and bismuth oxide, characterized by comprising silica, sulfur trioxide and aluminum oxide/red oxide.

In accordance with another aspect of the present invention, there is provided a self-neutralising type of calcium hydroxide preparation for use in dentistry, including an active silica material and bismuth oxide, characterized in that it comprises silica, sulfur trioxide and aluminum oxide/red oxide, and is hardened by addition of a physiological saline solution.

MODE FOR INVENTION

Hereinafter, preferred embodiments of the present invention will be described in detail so that a person of ordinary skill in the art can easily carry out the invention.

In order to prepare a self-neutralising calcium hydroxide preparation for use in dentistry in accordance with the present invention, it is first necessary to prepare a portland cement clinker (In this regard, a different type of cement clinker may be prepared, depending on specific circumstances). Herein, a clinker refers to a lump of agglomerates, in which part of the components are melted, and which are sintered to be porous. A clinker is also called a sintered lump. In general, a clinker is a small lump obtained by sintering a raw material of cement in a rotary kiln or the like, and the main components of a cement clinker is $3CaO.SiO_2$, $3CaO.Al_2O_3$, $2CaO.SiO_2$ and $4CaO.Al_2O_3.Fe_2O_3$.

A method of preparing a portland cement clinker in accordance with the present invention is as follows. First, clay including a large amount of alkaline materials such as silica ($SiO_2$), aluminum oxide ($Al_2O_3$) and red oxide ($Fe_2O_3$) is mixed with limestone and pulverized. Thereafter, silica and red oxide are further mixed into the mixture, which is then fired at approximately 1,450° C., to prepare a portland cement clinker in accordance with the present invention. In this case, it is desirable that the rate of the mixed clay ranges from 20% to 30%, approximately.

Next, preferably, an active silica material such as volcanic ash, silicate white clay and fly ash is mixed to the portland cement clinker by approximately 15% to 40%, and bismuth oxide is added and mixed thereto by approximately 30% or less. Herein, the numerical rates may be mass ratios (Surely, such rates may be volumetric ratios, but hereinafter, rates are to be understood as mass ratios. Numerical values of the two kinds of rates are (substantially) identical in a probable condition, but it is easier to control an experiment required for the present invention based on mass ratios). Alternatively, bismuth oxide may be added to artificial Pozzolan cement (or natural cement) by the same rate.

Further, bismuth oxide, which is additionally mixed to use the calcium hydroxide preparation for dental treatment, allows the self-neutralising calcium hydroxide preparation for use in dentistry to have a radiation contrast feature so that, after a tooth having dental caries is treated, the treated portion can be photographed by an X-ray in diagnosing the treated portion. As described above, the mixture quantity of bismuth oxide is no more than 30% based on a mass ratio. If more bismuth oxide is mixed, bioaffinity would deteriorate and it would give a bad influence on the physical properties of the self-neutralising calcium hydroxide preparation for use in dentistry. Thus, such mixture is to be avoided.

In this connection, bismuth oxide was mixed to Pozzolan cement by the rates of 20%, 14% and 11% (or the rates of 25%, 18.75% and 12.5%) and radio-opacity in each case was experimentally measured, to grasp the most appropriate mixture quantity of the bismuth oxide.

In the experiments, test samples having a diameter of 10 mm and a thickness of 1 mm, each having a different mixture ratio, were produced with Pozzolan cement and placed in an aluminum mold, and maintained at 37° C. and 96% humidity for three hours.

The experimental results show that, when bismuth oxide is mixed by a 20% (or 25%) mass ratio with the Pozzolan cement, it is not virulent to cells, and a highest radio-opacity is measured to have a value corresponding to aluminum having a thickness of 6.81 mm.

As such, in consideration of the bioaffinity, the radio-opacity and the physical stability of the self-neutralising calcium hydroxide preparation for use in dentistry, it is most desirable that bismuth oxide is mixed by a mass ratio of approximately 20% (or 25%).

To allow the self-neutralising calcium hydroxide preparation to be effectively used for dental treatment, such preparation has to have the following physical properties required for dental treatment. An excellent hardening feature, a compression tenacity and a volume stability are those physical properties required for a dental filler. Further explanations on these properties will be given in the following.

The self-neutralising calcium hydroxide preparation used as a filler for a tooth having progressive dental caries should be hardened as soon as possible after it is filled. Otherwise, the treatment time would be extended too much. Preferably, the self-neutralising calcium hydroxide preparation for use in dentistry in accordance with the present invention needs to start hardening within about five minutes at a room temperature (at about 20° C.) after an operation.

A filler-filled tooth serves to chew food. In particular, a user may feel relieved and tend to immediately have food with the self-neutralising calcium hydroxide preparation for use in dentistry being filled in his tooth, and thus, the filler needs to preferably have a compression tenacity of a certain degree at an initial stage after filling. Therefore, the self-neutralising calcium hydroxide preparation used for treating dental caries needs to show a compression tenacity of two mega pascal (MPa) or higher at a room temperature within fifteen minutes after an operation.

Further, a filler used for tooth treatment loses its volume due to contraction when a certain period of time has passed after the filler was applied to a tooth, the treatment was completed and the filler started to be hardened. If the volume loss of the self-neutralising calcium hydroxide preparation for use in dentistry filled in the treated portion of a tooth is significant, the coupling between the tooth and the self-neutralising calcium hydroxide preparation for use in dentistry becomes weak, and if worse, the filler may be separated from the tooth. Therefore, the filler needs to have a volume stability to some extent. For example, the contraction of the self-neutralising calcium hydroxide preparation for use in dentistry should be under 2,000 μm even after one month passed since the operation. Since the contraction of the self-neutralising calcium hydroxide preparation for use in dentistry in accordance with the present invention slows down one month after the start of hardening, it is important to keep under a certain degree the contraction for the first one month after the operation.

Besides, a tooth filler needs to have physical properties such as watertightness, which means not allowing for moisture infiltration when hardened after an operation, and chemical resistance, which means not reacting with a component contained in food or secretions from bacteria living in an oral cavity. Even though it is possible to use a special chemical for the hardening during an operation, it is desirable to use a physiological saline solution that does not affect a human body and is safe to utilize rather than such a special chemical. This is because a special chemical is expensive and harmful to a human body. Thus, the self-neutralising calcium hydroxide preparation for use in dentistry needs to have reactivity with a physiological saline solution.

To see the above physical properties, a chemical composition of silicon, aluminum and iron, which are additionally mixed with the self-neutralising calcium hydroxide preparation for use in dentistry, needs to have a certain composition ratio.

After repeated experiments, it is found that the self-neutralising calcium hydroxide preparation for use in dentistry in accordance with the present invention may be preferably derived by mixture with silica ($SiO_2$) of 17% or more, sulfur trioxide ($SO_3$) of 4% or less and $Al_2O_3.Fe_2O_3$ of 2% or more, based primarily on clayish limestone ($CaCO_3$). Herein, the mixture rates are all mass ratios.

Meanwhile, when the self-neutralising calcium hydroxide preparation for use in dentistry is used as a root canal filler for an endodontic treatment of an infected tooth, the treatment may need to be performed repeatedly, depending on a specific situation. In this case, the previously operated filler needs to be removed. Herein, if the hardness of the filler is too high, it would be difficult to remove the filler. To avoid this difficulty, it is desirable to reduce the hardness of the self-neutralising calcium hydroxide preparation for use in dentistry to a certain degree by mixing zinc oxide or titanium dioxide below 30%. In this case, the mixed zinc oxide or titanium dioxide has an anti-inflammatory effect and whitens the self-neutralising calcium hydroxide preparation for use in dentistry to conceal the treatment mark not to be exposed to others after the operation is finished on the tooth. However, in case the mixture ratio of zinc oxide or titanium dioxide is no less than 50%, the hardness of the self-neutralising calcium hydroxide preparation for use in dentistry decreases below a certain desired level, and thus, it is essential to be attentive to the mixture ratio.

The self-neutralising calcium hydroxide preparation for use in dentistry in accordance with the present invention constituted as described above is used for dental treatment according to the following process.

A tooth portion having progressive dental caries is removed, which may include a blood vessel tissue and a nerve tissue of a dental root as well as a tooth structure such as enamel and dentine, and the space caused by the removal is filled with the self-neutralising calcium hydroxide preparation for use in dentistry in accordance with the present invention.

When a certain amount of physiological saline solution is added to the self-neutralising calcium hydroxide preparation for use in dentistry in accordance with the present invention, clayish limestone, the primary base of Pozzolan cement, is hydrated to produce calcium hydroxide. Herein, water may be used in place of a physiological saline solution to produce calcium hydroxide, but it is desirable to use a physiological saline solution in consideration of its antibiotic disinfection effect.

The produced calcium hydroxide is combined with silica of the self-neutralising calcium hydroxide preparation for use in dentistry in accordance with the present invention to produce calcium silicate. Moisture, which is generated when calcium silicate is produced, reduces hydration heat and induces generation of a neutral material.

The reaction as above is expressed as follows:
The reaction as above is expressed as follows:

$$Ca(OH)_2 + SiO_2 \rightarrow CaO, SiO_2, H_2O \qquad \text{[Chemistry Formula 1]}$$

The space created in the tooth due to the treatment of the dental caries is filled with the self-neutralising calcium hydroxide preparation for use in dentistry in accordance with the present invention, to which a physiological saline solution is added. When the self-neutralising calcium hydroxide preparation for use in dentistry in accordance with the present invention is combined with moisture, it starts to be hardened within five minutes at a room temperature, and thus, an operation needs to be performed as soon as the physiological saline solution is added.

Further, in case infection at a lower portion of a dental root is progressive and a generic therapy is not effective, the self-neutralising calcium hydroxide preparation may be used to cure the infection. However, the self-neutralising calcium hydroxide preparation used for the curing may sometimes have too high hardness to be re-operated. Thus, to deal with this, it is desirable to adjust the hardness of the self-neutralising calcium hydroxide preparation for use in dentistry in accordance with the present invention by adding zinc oxide or titanium dioxide.

While the present invention has been described with respect to particular preferable embodiments as above, it is not limited to the embodiments. Without departing from the spirit of the present invention, various modifications and changes may be made by a person of ordinary skill in the art. It should be understood that such modifications and changes come under the scope of the following claims.

What is claimed is:
1. Pozzolan cement for dental treatment comprising active silica, bismuth oxide and a cement clinker produced from a mixture of clayish limestone, silica, red oxide and a clay comprising silica, sulfur and aluminum oxide/red oxide.

* * * * *